United States Patent [19]
Vnek et al.

[11] Patent Number: 4,578,217
[45] Date of Patent: Mar. 25, 1986

[54] SYNTHETIC ANTIGENIC PEPTIDE DERIVED FROM HEPATITIS B SURFACE ANTIGEN

[75] Inventors: John Vnek, Bronx; Alfred M. Prince, Pound Ridge; Hafeez Ikram, Corona, all of N.Y.

[73] Assignee: New York Blood Center, Inc., New York, N.Y.

[21] Appl. No.: 493,904

[22] Filed: May 12, 1983

[51] Int. Cl.$^4$ .......................................... C07C 103/52
[52] U.S. Cl. ............................................. 260/112.5 R
[58] Field of Search ................................ 260/112.5 R

[56] References Cited

U.S. PATENT DOCUMENTS

| | | | |
|---|---|---|---|
| 4,493,795 | 1/1985 | Nestor, Jr. et al. | 260/112.5 R |
| 4,493,796 | 1/1985 | Rinehart, Jr. | 260/112.5 R |
| 4,496,521 | 1/1985 | Lewis | 260/112.5 R |
| 4,499,080 | 2/1985 | Duflot et al. | 260/112.5 R |
| 4,499,081 | 2/1985 | Laerum | 260/112.5 R |

FOREIGN PATENT DOCUMENTS 0056249  7/1982  European Pat. Off. ..... 260/112.5 R

OTHER PUBLICATIONS

Journal of Medical Virology, 11, 115–124 (1983).
Journal of Virological Methods, 3, 349–354 (1982).
Journal of Virological Methods, 4, 177–185 (1982).
Intervirology, 16, 176–183 (1981).
Proceedings of the National Academy of Sciences, 79, No. 13 (1982) pp. 4400–4404.
Molecular Immunology, 18, No. 9, pp. 869–872 (1981).
C. R. Acad. Sc. Paris, 292, 26 Jan. (1981) 373–8.
Proceedings of the National Academy of Sciences, (1981) 78, 3824–3828.
Molecular Immunology, 18, 237–244 (1981).

Primary Examiner—Delbert R. Phillips
Attorney, Agent, or Firm—Sprung Horn Kramer & Woods

[57] ABSTRACT

There is disclosed a new synthetic peptide which evokes an immunological response. The synthetic peptide, moreover, interacts with antibodies to hepatitis B surface antigen (HBsAg). Thus, the synthetic peptide is useful as an immunizing agent in a vaccine as an active component thereof where it serves to produce antibodies in vivo which are protective against hepatitis B virus. The synthetic peptide of the invention comprises the following sequence of amino acids: Arg Trp Met Met Leu Arg Arg (I) and preferably has the following sequence: Gly Tyr Arg Trp Met Met Leu Arg Arg Phe Gly (II).

2 Claims, 2 Drawing Figures

FIG. 1B

SYNTHETIC ANTIGENIC PEPTIDE DERIVED FROM HEPATITIS B SURFACE ANTIGEN

BACKGROUND OF THE INVENTION

1. Field of the Invention

This invention relates to a synthetic peptide, to a synthetic vaccine comprising said peptide, to an agent for stimulation of antibody production to a naturally occurring antigen, and to a process for their preparation.

2. Discussion of Prior Art

Hepatitis B virus (HBV) vaccines have been prepared from lipoprotein particles containing hepatitis B surface antigen (HBsAg) isolated from plasma of chronic HBV carriers (McAuliffe et al., 1980). This source of antigen is costly and scarce, therefore research was initiated to produce the immunogen by recombinant DNA technology. Despite extensive efforts, the yield of immunogenic material has been disappointing (Burrell et al., 1979; Edman et al., 1981, Mackay et al., 1981). Only recently cloning the HBsAg gene led to production of lipoprotein particles of full immunogenic potency in *S. cerevisiae* (Valenzuela et al., 1982). However, for practical purposes, the yield of HBsAg particles was still very low. Therefore, several groups of workers have attempted to develop a synthetic hepatitis B vaccine searching by computer the amino acid sequence of HBsAg for continuous antigenic sites (Atassi, 1980), either indirectly by exclusion of hydrophobic sequences (Vyas et al., 1981; Lerner et al., 1981; Dreesman et al., 1982) or by direct search for hydrophilic structures (Hopp and Woods, 1981; Hopp, 1981; Prince et al., 1982).

It has been reported that when the DNA for the HBsAg gene is split into approximately two equal halves and cloned in E. coli, it produces two separate antigenic peptides (Mackay et al., 1981). This information has been confirmed by synthesis of antigenic (immunogenic) peptides derived both from the C-terminal (Lerner et al., 1981; Dreesman et al., 1982; Hopp and Woods, 1981; Hopp, 1981; Prince et al., 1982, Bhatnagar et al., 1982) and from the N-terminal (Lerner et al. 1981) halves of the HBsAg molecule. When the above synthetic peptides were mapped on a diagram of hydrophilicity of their amino acid residues, it was determined that practically all the peptides comprising the prominent hydrophilic domains in the sequence of HBsAg have already been synthesized (results not shown).

SUMMARY OF THE INVENTION

We have now discovered a new synthetic peptide which evokes an immunological response. The synthetic peptide, moreover, interacts with antibodies to hepatitis B surface antigen (HBsAg). Thus the synthetic peptide is useful as an immunizing agent in a vaccine as an active component thereof where it serves to produce antibodies in vivo which are protective against Hepatitis B virus.

The synthetic peptide of the invention comprises the following sequence of amino acids:

Arg Trp Met Met Leu Arg Arg  (I)

Preferably the synthetic peptide has the following sequence

Gly Tyr Arg Trp Met Met Leu Arg Arg Phe Gly  (II)

Such preferred synthetic peptide includes the hydrophobic N-terminal and C-terminal residues (tyrosine and phenylalanine, respectively) as well as a pair of terminal glycyl residues in the N-terminal and in the C-terminal positions. The glycyl residues are especially useful where the synthetic peptide is to be chemically connected to a carrier substrate such as a physiologically compatible carrier. When disposed on such carriers, the synthetic peptide is useful as a vaccine for active immunization against hepatitis B virus.

The synthetic peptide of formulae I or II supra can be part of a larger or longer chain, including a longer amino acid sequence. It is preferred, however that any amino acid chain containing this synthetic peptide not exceed 50 amino acids. Preferably the amino acid sequence does not exceed 40 amino acids and still more preferably it does not exceed 30 amino acids. Very suitable are sequences containing less than 20 amino acids, especially less than 15 amino acids. This heptapeptide of the invention (Formula I) or its extended undecapeptide (Formula II) can be disposed on a non-amino acid containing chain (e.g. polyethylene glycol, PEG or its derivatives).

The synthetic vaccine is prepared either by chemically synthesizing a chain of amino acids corresponding to the sequence of amino acids given supra. The amino acid chain so obtained can thereafter, for use as a vaccine, be disposed on a physiologically acceptable carrier, which can be a polymer itself. The resultant composition can thereafter be diluted with a physiologically acceptable medium. The composition is then ready for introduction into a host animal. The synthetic peptide can also be immobilized on a soluble or insoluble substrate such as Sepharose when it is intended to employ the same as a diagnostic agent.

It will be realized that the synthetic vaccine of the invention can contain a single or a plurality of sequences given above and can be disposed in an amino acid chain containing antigenic determinants corresponding to other viruses or allergens. Similarly, the synthetic vaccine can contain a plurality of amino acid sequences of different antigenic determinants of multiple known or unknown protein antigens or allergens. Thus the synthetic vaccine can contain a plurality of a single antigenic determinant or can contain a single amino acid sequence of a first antigen and another of a second antigen or allergen.

Where the synthetic peptide of the invention is part of a long chain, such as when there are more than one immunologically active amino acid sequence in the chain, the chain can contain residues of any of the following moieties: segments of polyamino acid, polysaccharides, polyamides, vinyl polymers, ester polymers, polyacetals, polyolefins, polyphenyl sulfides, polycarbonates as well as bivalent organic radicals, including bivalent alkylene and other saturated or unsaturated organic compounds e.g. hydrocarbon radicals. These residues can have molecular weights of up to 1,000,000, preferably between 10,000 and 100,000, the molecular weight being determined by ultracentrifugation.

It will be realized that a chain containing the synthetic peptide can contain a vaccine adjuvant. Such vaccine adjuvants include muramyl dipeptide and its analogs which can be covalently bonded.

Alternatively, the vaccine can comprise a chain of amino acids containing one or more sequences of the synthetic peptide together with other chains of amino acids containing the same synthetic peptide or different synthetic peptides corresponding to different antigens or allergens. These additional chains can be of the same or different chain length. The chains which contain synthetic peptide sequences can be interconnected with one another such as by crosslinking or by being bonded directly thereto in the form of a branched chain, or the respective chains are bonded to a central "carrier". It is contemplated that the vaccine contain a plurality of the same or different synthetic peptide sequences of the invention. In particular, it is contemplated that a vaccine contain between 1 and 1,000 of such sequences, per covalent unit. It can also have present in addition thereto between 1 and 1,000 peptide sequences per covalent unit of a different antigen or allergen or plurality of different antigens or allergens, all as desired.

The synthetic peptide of the invention requires proper presentation in order to elicit an immune response. To this end, a carrier is provided therefor. The "carrier" is simply a physiologically acceptable mass to which the synthetic peptide is attached. A carrier can comprise a chain of amino acids or other moieties and to that end it is specifically contemplated to use as a carrier a dimer, oligomer, or higher molecular weight polymer of sequences containing amino acids of the synthetic peptide. Thus the synthetic peptides can be polymerized to build up a chain of two or more repeating units so that repeating sequences serve both as "carrier" and immunologically active site. States differently, an independent carrier is not required. It is preferred that alternative carriers comprise some substance, animal, vegetable, or mineral, which is physiologically acceptable and functions to present the synthetic peptide so that it is recognized by the immune system of a host and stimulates a satisfactory immunological response. Thus, a wide variety of carriers are contemplated, and these include materials which are inert, which have biological activity and/or promote an immunological response. For instance, proteins can be used as carriers and there is included within such subclass, human serum proteins, tetanus toxoid, etc.

Polysaccharides are also contemplated as carriers, and these include especially those of molecular weight 10,000 to 1,000,000, including in particular starches, dextran, agarose, ficoll or its carboxy methyl derivatives and carboxy methyl cellulose.

Polyamino acids are also contemplated for use as carriers and these polyamino acids include, among others, polylysine, polyalanyl polylysine, polyglutamic acid, polyaspartic acid and poly ($C_2$–$C_{10}$) amino acids.

Vaccines can be used as carriers for the synthetic peptide provided by the invention. In other words, the synthetic peptide residues provided by the invention can themselves be attached to other vaccines including vaccines for measles, influenza, smallpox, polio, diphtheria, pneumonococci, meningococci, and the like.

Organic polymers can be used as carriers, and these polymers include polymers and copolymers of amines, amides, olefins, vinyls, esters, acetal, polyamides, carbonates, ethers, phenylene sulfides, silicones, urea formaldehyde condensation products, phenol formaldehyde condensation products, urethanes, melamine formaldehydes, epoxy resins, acrylic resins, allyl resins, and the like. Generally speaking, the molecular weight of these polymers will vary dramatically. The polymers can have from two repeating units up to several thousands e.g., two thousand repeating units. Of course, the number of repeating units will be consistent with the use of the vaccine in a host animal. Generally speaking, such polymers will have a lower molecular weight, say between 10,000 and 100,000, determined in accordance with the procedure set forth above.

Inorganic polymers can also be employed. These inorganic polymers can be inorganic polymers containing organic moieties. In particular, silicates can be used as carriers. It is preferred that the carrier be one which is an immunological adjuvant. In such cases, it is particularly contemplated that the adjuvant be any one of the following: muramyl dipeptide or its analogs.

The carrier can also be the residue of a crosslinking agent employed to interconnect a plurality of peptides containing chains. The crosslinking agent can be one which interconnects the chains at a point containing the sequence of the synthetic peptide amino acids. Alternatively, the crosslinking agent can interconnect a plurality of chains at a point other than where the synthetic peptide is located. Crosslinking agents which are contemplated include crosslinking agents which have as their functional group an aldehyde, carboxyl, amine, amido, imido or azidophenyl, group. In particular, there is contemplated the use of glutaraldehyde as a crosslinking agent, a divalent imido ester or a carbodiimide. Particularly contemplated divalent imido esters are those of the formula wherein m is 1 to 13 and R is an alkyl group of 1 to 4 carbon atoms.

Particularly contemplated carbodiimides for use as crosslinking agents include cyclohexylcarbodiimide, ethyldimethylaminopropyl carbodiimide, N-ethylmorpholino cyclohexyl carbodiimide, diisopropyl carbodiimide, etc.

It should be understood that the vaccine of the invention can be in admixture with other proteins and these proteins include the proteins of known antigens or allergens. Thus, when it is stated herein that the vaccine is characterized by the absence of an amino acid sequence corresponding to the entire protein antigen or allergen it is meant that notwithstanding the absence of the amino acid sequence of the entire protein antigen or allergen, the composition functions as a vaccine, i.e. provides protective immunization by formation of antibodies in the case of an antigen or a lessening of allergic sensitivity in the case of an allergen.

In addition to the carriers named above, or as an alternative thereto we can use a carrier comprising a straight or branched substituted or unsubstituted, saturated or unsaturated hydrocarbon residue of at least twelve carbon atoms as disclosed in copending application Ser. No. 358,150 of Thomas P. Hopp, assigned to the assignee hereof, the disclosure of which is thereby incorporated herein by reference. As disclosed therein, in particular, the carrier is one having at least twelve carbon atoms in a chain whose chain is either an alkyl or alkenyl group. Such alkyl or alkenyl group can have up to 36 carbon atoms but is preferably in the range of $C_{12}$ to $C_{24}$. These hydrocarbon residues can be provided by fatty acids by simple coupling of the fatty acid moiety to a terminal functional group of the synthetic peptide by relatively routine chemistry. There is contemplated, however, carrying the synthetic residue on such hydrocarbon residues without the use of the carboxylic acid functional group of the fatty acid whereby the synthetic peptide is joined to the hydrocarbon residue without a carbonyl connecting link.

Thus, out invention can be described broadly as a composition comprising a synthetic peptide of the sequence given supra in combination with a specific carrier as represented by the formula (free terminal amino group)

wherein m is 0 or 1:

R is a substituted or unsubstituted alkyl or alkenyl radical of at least 12 carbon atoms; and Peptide is the residue of formulae I or II, supra.

Referring to the formula above we can couple the synthetic peptide moiety to an alkyl or alkenyl group of at least 12 carbon atoms by blocking all those amino groups of the synthetic peptide residue so that they are free of reactivity to a carboxylic acid except that a terminal amino group remains available for reaction. The terminal amino group of the synthetic peptide then reacts with a moiety which supplies a carboxylic acid group whereby condensation of a hydrogen atom of the amino group with the hydroxyl group of carboxylic acid group (dehydration) effects interlinkage of the synthetic peptide with the carboxylic acid group in accordance with the following equation:

In accordance with this reaction there is formed a composition as defined in equation I above wherein m=1. Also envisaged, however, in disposing these synthetic peptides on a $C_{12}$–$C_{36}$ alkyl or alkenyl moiety without using a carboxylic acid or similar functional group to link with the terminal amino group. Thus, for instance, there is contemplated a substitution reaction in accordance with the following equation:

in which case there is formed a synthetic vaccine within formula I above wherein m is 0. Numerous alternative routes to disposing a synthetic peptide on a $C_{12}$ to $C_{36}$ alkyl or alkenyl group are apparent; these invariably linking the synthetic peptide to the alkyl or alkenyl moieties via a terminal amino group of the synthetic peptide moiety.

In forming a synthetic vaccine in accordance with this invention, it is preferred to use a fatty acid of $C_{12}$ to $C_{24}$. Particularly contemplated fatty acids include the following Palmitic
Stearic
Behenic
Oleic The synthetic peptide can be prepared using the Merrifield solid phase procedure to build up the appropriate sequence of L-amino acids from the carboxyl terminal amino acid to the amino terminal amino acid. Starting with the appropriate carboxyl terminal amino acid attached to a polystyrene or other appropriate resin via chemical linkage to a chloromethyl group, benzhydrylamine group, or other reactive group of the resin, amino acids are added one by one using the following procedure for each:

(a) peptidyl resin is washed with methylene chloride;
(b) neutralized by mixing for 10 min. at room temperature with 5% (v/v) diisopropylethylamine (or other hindered base) in methylene chloride;
(c) washed with methylene chloride;
(d) an amount of amino acid equal to six times the molar amount of the growing peptide chain is activated by combining it with one-half as many moles of a carbodiimide (e.g. dicyclohexylcarbodiimide, diisopropylcarbodiimide, etc.) for 10 minutes at 0° C., to form the symmetric anhydride of the amino acid. The amino acid used should be provided originally as the N-α-butyloxycarbonyl derivative, with side chains protected with benzyl esters (aspartic and glutamic acids) benzyl ethers (serine, threonine, cysteine, tyrosine), benzyloxycarbonyl groups (lysine) or other protecting groups commonly used in peptide, synthesis;
(e) the activated amino acid is reacted with the peptidyl resin for 2 hours at room temperature, resulting in addition of the new amino acid to the end of the growing peptide chain;
(f) the resin is washed with methylene chloride;
(g) the N-α-butyloxycarbonyl group is removed from the most recently added amino acid by reacting with 30% (v/v) trifluoroacetic acid in methylene chloride for 30 minutes at room temperature.
(h) the resin is washed with methylene chloride;
(i) steps (a) through (h) are repeated until the required peptide sequence has been constructed.

The peptide is then removed from the resin and simultaneously the side-chain protecting groups are removed, by reacting the anhydrous hydrofluoric acid containing 10% (v/v) of anisole. Subsequently, the peptide can be purified by gel filtration, ion exchange or high pressure liquid chromatography, or other suitable means.

In some cases, chemical synthesis can be carried out without the solid phase resin, or on soluble carriers e.g. polyethylene glycol or derivatives thereof, in which case the synthetic reactions are performed entirely in solution. The reactions and the final product are otherwise essentially identical.

The Merrifield solid phase synthesis for synthetic peptides is a particularly desirable approach to formation of a fatty acid carried synthetic peptide, since it provides a convenient means for attachment of the carrier in accordance with the invention, although it should be understood that liquid phase approaches can also be employed. The Merrifield solid phase approach involves connecting amino acids to one another where the pendent reactive groups, e.g., amino, hydroxyl, carboxyl, imidazol groups, are blocked. After the final amino acid has been coupled, the N-terminus is deblocked and a fatty acid or other suitable lipophilic substituent or component supplying a $C_{12}$ to $C_{36}$ alkyl or alkenyl group is reacted by procedures outlined above for use in amino acid couplings, the procedure is carbodiimide mediated peptide (amide) bond formation, hydroxybenzotriazole ester addition or addition of a fatty acid symmetrical or asymmetrical anhydride.

This results in a peptide with covalent N-terminal fatty acid or similar moiety. The peptide is then removed from the resin by typical hydrofluoric acid treatment, and purified if necessary.

Analogously, one can form chains containing a plurality of the synthetic peptides of the invention or with amino acid sequences corresponding to different antigens or allergens by the following technique: An aqueous solution of the synthetic peptide or peptides is mixed with a water-soluble carbodiimide (e.g. ethyl-dimethylaminopropylcarbodiimide). This results in polymerization of the peptide(s); depending on the use of the side chain blocking groups mentioned above, either straight chain or branched polymers of the synthetic peptide can be made.

If desired, the synthetic peptide containing chain employed in the vaccine of the invention can have bonded thereto a chain of any of the following moieties: polypeptide, polyaminoacid, polysaccharide, polyamide, polyacrylamide which can serve as a stabilizing chain or as a bridge between synthetic peptide sequences. Such chains are available commercially or, in the case of polyamino acids, are formed by a process which comprises: mixing a solution of epitope synthetic peptide with a solution of the N-carboxylanhydride of the amino acid and allowing a base-catalyzed polymerization to occur, which is initiated by the amine groups of the peptide.

The disposition of a chain or chains on a "carrier" is effected as follows:

1. Protein Carrier. The protein and the synthetic peptides are dissolved together in water or other suitable solvent, and covalently linked via amide bonds formed through the action of a carbodiimide. The resulting product may contain one or more copies of the peptide per protein monomer.

2. Polysaccharide Carriers: Oligosaccharide carriers should have molecular weights in the range of 1,000 to 1,000,000. In order to covalently link these to H-epitope peptides, suitable functional groups must first be attached to them. Carboxyl groups may be introduced by reacting with iodoacetic acid to yield carboxymethylated polysaccharides, or by reacting with carbonyldiimidazole to yield activated carbonyl esters. Carboxymethyl polysaccharides are coupled to the peptide by a carbodiimide reaction, while the activated carbonyl esters react spontaneously with peptides. Multiple copies of the synthetic peptide should be attached to each oligosaccharide unit.

3. Polyamino Acid Carriers. These carriers should have molecular weights in the range 1,000 to 1,000,000. Polylysine and polyornithine have primary amino groups on their side chains; polyaspartic acid and polyglutamic acid have carboxyl groups. Peptides may be coupled to these via amide bonds using the carbodiimide reaction. Another carrier that provides amino groups for coupling is polylysine to which polyalanine has been attached to the side chains of the lysine residues. The synthetic peptide may be attached to the ends of the polyalanine chains, also by a carbodiimide reaction. Multiple copies of the synthetic peptide should be attached to each oligopeptide unit.

The respective synthetic peptide containing chains can be linked to one another by a cross-linking agent. Generally speaking, the cross-linking agent can be any one of a type identified above. Crosslinking is effected by reacting the synthetic peptide containing residue with the crosslinking agent as follows:

Reaction with glutaraldehyde or a bis-imidate (e.g. dimethylsuberimidate) in aqueous solution results in polymerization of the synthetic peptide containing moiety with the crosslinking reagent forming covalent bridges between peptide monomers.

By the procedure of the invention there is realized a vaccine which can be characterized by the absence of an amino acid sequence of the entire protein antigen or allergen. The hepatitis B vaccine can be synthesized free of other peptide sequences of the hepatitis B surface antigen protein, or other proteins found in the virion. Vaccines can be synthesized which are free of biologically produced components, free of viral components whether they are active or inactive, free of antibodies, free of deoxyribonucleic acid (DNA) and free of lipids, and are, therefore, likely to be substantially free from undesirable side effects commonly found with other vaccines (unintentional infection with virus, allergic reactions, fevers, etc.).

The synthetic vaccines are characterized by exceptional specificity and evoke an unusual and special response when introduced into a host animal. Whereas a vaccine made of natural material and introduced into a host animal usually evokes an immunological response by the reaction of antibodies specific to a number of distinct epitopes present on the antigens found in that vaccine, when the vaccine of the present invention is introduced into a host animal, it causes the formation of antibodies which are mono-specific, i.e., are specific to the single antigenic site on the vaccine. The synthetic peptide produced not only antibodies to a single specific antigenic determinant on the natural virus but also produce a mixture of antibody molecules, all of which are specific to that same antigenic determinant. Hence, the antibodies of the invention are "hetero-molecular". This provides different molecules all of which are suitabe to bind the natural virus or allergen. Some of these molecules due to their size, shape, mobility and hydrophilic/hydrophobic properties may act faster or more strongly than others. This insures broad and specific protection.

It is to be realized, moreover, that the antibodies are "mono-specific" in a different sense than are antibodies produced from compositions containing the entire or virtually the entire amino acid sequence of the natural viral protein. The latter produce antibodies to a plurality of different antigenic determinants of the same virus but not to other viruses. Thus, while being "mono-specific" in the sense of producing antibodies only to that virus they produce antibodies which are not specific to a single antigen determinant of the virus.

Thus the synthetic peptide of the invention can be used to form immune globulins comprising the single antigenic determinant specific heteromolecular antibodies of the invention. These antibodies can be produced in animals such as chimpanzees. They serve as diagnostic agents where due to their heteromolecular but single determinant specific component they insure a response to naturally occurring virus in a test serum. Thus they can be used in serological testing to identify the presence of Hepatitis B virus.

In the preparation of a vaccine the concentration of the same in the physiologically acceptable medium will vary depending on the number of synthetic peptides or other residues therein. Generally speaking, the active component of the vaccine can be present in a concentration which is lower than the concentration of active material in known vaccines since in the known vaccines, higher concentrations were required in order to have present the required number of antigenic determinants to evoke the desired immunological response. The vaccine concentration will, of course, vary from vaccine to vaccine. Generally speaking, its concentration will be from 5 to 1,000 µg, preferably 20 to 50 µg per dose to give suitable immunogenicity. It is particularly contemplated to use the vaccine in a dosage of 1 to 100 µg., especially 1 to 20 µg. per dose.

The HBsAg vaccine will have sufficient potency to provide an anti-$HB_s$ titer of at 100 milli-international units (MIU) in comparison to the WHO International HBIG Standard in at least four chimpanzees immunized with 2 doses of the standard vaccine in accordance with the recommended schedule, the anti-$HB_s$ remaining detectable at a titer of greater than 10 mIU for at least a year following the onset of immunization of the chimpanzees. Naturally, the vaccine concentration can vary from these concentrations in accordance with the desired effect.

The vaccine can be administered by subcutaneous or intramuscular injection. While the preferred route depends upon the particular vaccine, intramuscular injection is generally suitable. Frequency of administration depends upon the vaccine and the number and type of synthetic peptide moieties and their concentration in the active component. Generally speaking, the vaccine is administered in two doses about one month apart followed by a booster at six months to one year after primary immunization. Of course, the dosage depends upon the size of the host animal being inoculated. The subsequent doses or the booster depends on the level of antibody in the blood as a result of the initial immunization. Licensable adjuvants conventionally employed in vaccine manufacture can be utilized.

In the case of the hepatitis vaccine of the invention, the same is recommended for all persons at risk of developing hepatitis B infection and particularly those at especially high risk such as patients and staff on hemodialysis unit, medical personnel, persons of tropical populations and those visiting the tropics. In the case of tropical populations, particularly in Africa, Asia, the Medeterranean region and South America, where high incidence of hepatitis B infections has been consistently observed, the vaccine should be administered sufficiently early in life to prevent acquisition of chronic carrier state infection which tend to occur in these regions within the first five years of life. In fact, the vaccine is useful for all persons not already protected against hepatitis B infections as a result of prior immunity.

BRIEF DESCRIPTION OF DRAWINGS

Referring to the annexed drawings, all of which are graphs plotting one function or observation against another.

In order to more fully illustrate the invention and the manner of practicing the same, the following examples are presented.

EXAMPLES

Chemicals and Reagents

Chemicals were of analytical grade or otherwise specified The synthetic polypeptide carrier Poly-D,L-Alanyl-Poly-L-Lysine (A,L: M.W. 60,000) was purchased from Miles Laboratories (Elkhart, Ind.). Tetanus toxoid (Lot No. CPTxd-35) was a gift from Dr. George Grady (Biological Laboratories. The Commonwealth of Massachusetts). The monoclonal antibodies were acquired from Dr. Courouce of the National Blood Transfusion Center, Paris.

Peptide Synthesis

The peptide was synthesized in a liquid phase using as a carrier polyethylene glycol 5000 (PEG) derivatized with p-hydroxymethyl-benzoic acid (Bayer and Mutter, 1974). The peptide was released from the C-terminal esteric bond with PEG by saponification and deprotected according to a published procedure (Kito et al., 1980).

Peptide Analysis

The purified peptides were analyzed by TLC on silica gel plates with two solvent systems composed of BuOH-Pyridine-AcOH-$H_2O$ mixed in a ratio (v/v) of 5:5:1:4 and 30:20:6:24 respectively. The amino acid composition was determined after acid hydrolysis (6N HCl, 110° C., 24 hrs.) in a Beckman Model 119 Amino Acid Analyzer.

Coupling of Purified Peptides to Carriers by Carbodiimide

The original PEG-peptide and the free peptide (released from PEG) was coupled either to tetanus toxoid (TT) or to a synthetic polypeptide carrier (A,L) with carbodiimide in the following molar ratios: TT-peptide-PEG 1:50; TT-peptide 1:50; and A,L-peptide 1:2, according to published procedures (Bauminger and Wilchek, 1980; Goodfriend et al., 1964, Nash et al. 1980).

Immunization of Animals

Three groups of Balb/c mice (10 in each) obtained from Jackson Laboratory (Bar Harbor, Maine) were injected subcutaneously on day 1 with 25 µg of the original PEG-peptide coupled to tetanus toxoid hereinafter (TT-peptide-PEG) or with 5 µg of the free peptide coupled so tetanus toxoid (TT-peptide) or the peptide synthetic carrier conjugate, (A, L-peptide) in 0.1 ml of 0.15M NaCl, 0.01M Phosphate pH7.2 (PBS) mixed with an equal volume of Freund's complete adjuvant (CFA). The mice were boosted with the same amount of conjugates suspended in incomplete Freund's adjuvant (IFA)

30 days after the primary inoculation. The animals were bled from the tail vein 30 and 60 days respectively after the primary inoculation.

Two white New Zealand rabbits were injected subcutaneously with 50 µg of peptide (based on the free peptide) conjugated to tetanus toxoid in 0.25 ml PBS mixed with an equal volume of CFA on day 1 and boosted with the same amount of sample mixed with IFA 30 days after the primary inoculation. The rabbits were bled weekly from the marginal ear vein.

IMMUNOLOGICAL ASSAYS

Competition RIA for a Peptide Conjugate

The antigenic activity of the peptide-synthetic carrier conjugate (A,L-peptide) was determined by competition RIA using $^{125}$I-HBsAg as follows:

The wells in a microtitration plate were coated directly by incubation with 50 µl of supernatant media (diluted 1:10 in PBS) from each of the hybridoma cell cultures for 2 hours at 37° C. and overnight at 4° C. After recovering the antibody the wells were washed 3× with PBS and incubated for additional four hours at 37° C. with 100 µl of 1% bovine serum albumin (BSA) in PBS (containing 10% Ausab negative control serum). The wells were washed again with PBS and used directly for the assay as follows: A 50 µl volume of the conjugate (100 µg/ml; based on the peptide moiety) suspended in negative control serum was mixed with 50 µl of $^{125}$I-HBsAg (Ausab reagent diluted 1:10 in negative control serum) in an antibody coated dilution plate. After incubation at room temperature overnight, the plates were washed and the individiual wells cut out and counted in a gamma counter. The results were expressed as percent of reduction of cpm in the presence of the conjugated peptide against the total cpm in the controls.

Determination of anti-HBs by RIA

The anti-HBs titers of sera were determined under standard conditions using the AUSAB reagents (Abbott Laboratories). Aliquots of 2×0.1 ml of sera (diluted with an equal volume of negative control sera) and 2×0.2 ml of rabbit sera were used for the assay. The titers were expressed either as ratio units of cpm of samples to cpm of negative controls (P/N) or the results were quantitated in comparison to the WHO International HBIG Standard and expressed as milli-international units (mIU) according to a published procedure (Wainfan, 1976).

Determination of Anti-Peptide Titers by ELISA

The anti-peptide antibody titers were determined by ELISA using commercial reagents (New England Nuclear and DAKO Corp.) The wells in a microtitration dilution plate were coated with 100 µl of the synthetic peptide (peptide-PEG) at a concentration of 100 µg/ml and 50 µl of serial 2-fold dilutions of sera were applied. Antibody binding was detected as described by Bittle et al (1982). The plates were read at 492 nm in a MICROELISA MRJ80 (DYNATECH Corp.) automatic plate reader and the values presented are expressed as reciprocals of the serum dilution showing at least 50% maximal O.D. reading.

RESULTS

The purified original PEG-peptide and the free peptide (released from PEG) were homogeneous when tested by TLC in two different solvent systems (see Methods). The amino acid composition of the peptide determined after acid hydrolysis (not corrected for decomposition) was the following: Leu: 1.0(1); Phe: 1.0(1); Gly: 1.7(2); Met: 1.6 (2); Tyr: 0.9 (1); Arg: 2.8 (3); Trp; not determined (should be 1). The numbers in parentheses represent the theoretical number of residues. These results are in agreement with the expected amino acid sequence: Gly-Tyr-Arg-Trp-Met-Met-Leu-Arg-Arg-Phe-Gly.

The results of immunization summarized in Table 1 show a rather weak slowly increasing anti-HBs responce in mice injected with the original PEG peptide coupled to tetanus toxoid (TT-Peptide-PEG). When the free peptide (released from PEG) coupled to tetanus toxoid (TT-peptide), or to the synthetic carrier (A,L-peptide) were injected into mice, both conjugates showed a fairly strong immune response (eight of ten mice responded). There was an approximately two-fold increase in titers after the second injection indicating a relatively weak boosting effect.

Figure 1A:
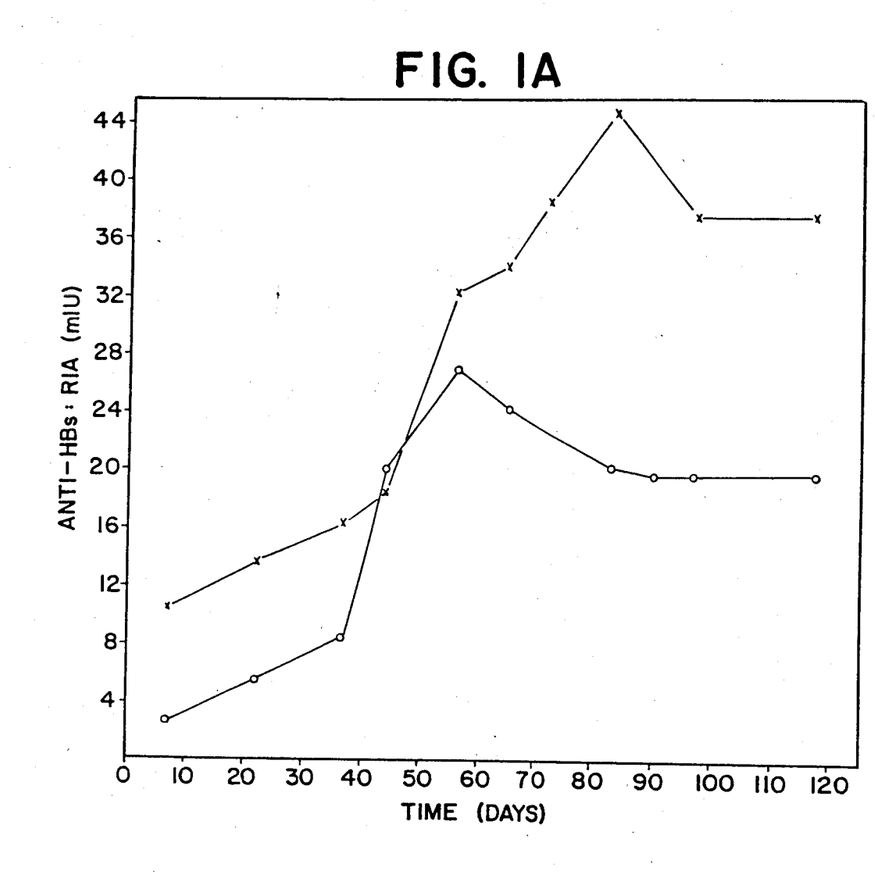
FIG. 1A is a time course diagram of anti-HBs response in rabbits injected with the peptide conjugated to tetanus toxoid as discussed below.
Figure 1B:
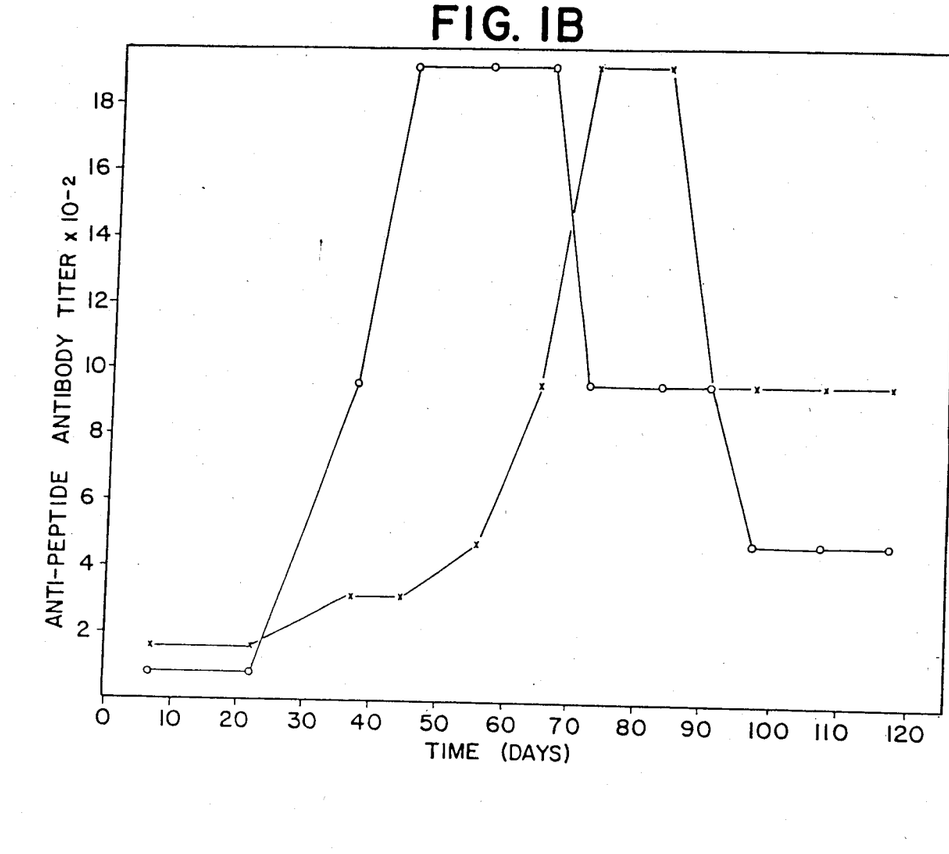
FIG. 1B is the anti-peptide antibody profile of sera collected from rabbits inoculated with the peptide conjugated to tetanus toxoid.

When the peptide-tetanus toxoid conjugate was injected into two rabbits both elicited a fairly strong anti-HBs response (FIG. 1A). The same sera analyzed for anti-peptide titers by ELISA (Bittle et al., 1982) showed a pattern similar to anti-HBs (FIG. 1B).

The ability of the conjugates to bind with monoclonal antibodies was tested by a microtitration plate RIA in competition with $^{125}$I-labeled purified HBsAg. A total of 19 different monoclonal antibodies were used but only five coated adequately. The peptide-synthetic carrier conjugate showed a positive reaction (>50% inhibition) in plates coated with 4 of 5 of the antibodies which could be tested (Table 2). These results indicate that the peptide carries an antigenic determinant which interacts with monoclonal antibodies produced against the components of the naturally occurring virus. Thus the purely synthetic peptide whose amino acid sequence is a derivative of a short sequence of the natural antigen is immunologically active with such naturally produced antibodies.

TABLE 1

| ANTI-HBs TITERS IN MICE IMMUNIZED WITH PEPTIDE-CARRIER CONJUGATES | | |
|---|---|---|
| Immunizing Preparation | Amount per Mouse (µg) | Range of Antibody Titers (P/N)* |
| | | Day 30 | Day 60 |
| TT—peptide-PEG | 25 | 2.1–4.8 (4) | 2.5–7.7 (7) |
| TT—peptide | 5 | 2.9–16.2 (8) | 2.6–33.2 (8) |
| A,L-peptide | 5 | 3.0–8.7 (8) | 3.3–17.7 (8) |

*Only positive titers are listed. Numbers in parenthesis represent number of mice responding out of the ten mice in each group.

TABLE 2

| MICROTITRATION PLATE COMPETITION RIA FOR A,L-SYNTHETIC-PEPTIDE USING MONOCLONAL ANTI-HBs ANTIBODIES | | | |
|---|---|---|---|
| Number | Monoclonal Antibodies | Antibody* Titers (P/N) | Percent Inhibition |
| 1 | 16-A8 | 16.0 | 69.3–70.6 |
| 2 | 20-A20 | 54.7 | 57.3–62.6 |
| 3 | 20-A92 | 49.6 | 51.2–60.1 |
| 4 | 107-A3 | 19.2 | 6.6–18.5 |
| 5 | 112-A51 | 16.4 | 59.1–79.4 |

*The amount of antibody coating the wells was determined under the same conditions as in the samples except for using 50 µl of the $^{125}$I—HBsAg reagent diluted directly with 50 µl of negative serum (see Methods).

| GLOSSARY | |
| --- | --- |
| Amino Acid | Abbreviation |
| Arginine | Arg |
| Glycine | Gly |
| Methionine | Met |
| Isoleucine | Ile |
| Leucine | Leu |
| Tyrosine | Tyr |
| Phenylalanine | Phe |
| Tryptophan | Trp |

BIBLIOGRAPHY

Atassi, M. Z. (1980) Precise determination of protein antigenic structures has unravelled the molecular immune recognition of proteins and provided a prototype for synthetic mimicking of other protein binding sites. Mo. Cell. Biochem. 32, 21–43.

Bauminger, S. and Wilchek, M. (1980) The use of carbodiimides in the preparation of immunizing conjugates. In Methods of Enzymology (Edited by van Vunakis, H. and Langone, J. J.) p. 151, Academic Press, New York.

Bayer, E. and Mutter (1974) Synthese des biologisch activen Undecapeptide Subtanz P nach der Flussig-Phasen-Methode. Methode. Che.M.Ber. 107, 1344–1352.

Bhatnagar, P. K. Pappas. E., Blum, H. E., Milich, D. R., Nitecki, D., Karels, M. J. and Vyas, G. N. (1982) Immune response to synthetic analogues of hepatitis B surface antigen specific for the a determinant. Proc. Proc. Natl. Acad. Sci. U.S.A. 79, 4400–4404.

Bittle, J. L., Houghten, R. A., Alexander, H, Shinnick, T. M., Sutcliffe, J. G., Lerner, R. A., Rowland, D. J. and Brown, F. (1982) Protection against foot-and-mouth disease by immunization with a chemically synthesized peptide predicted from the viral nucleotide sequence. Nature 298, 30–33.

Burrell, C. J., Mackay, P., Greenway, P. J., Hofschneider, P. H. and Murray, K. (1979) Expression in Escherichia coli of hepatitis B virus sequences cloned in pBR322. Nature 279, 143–147.

Dreesman, G. R., Sanchez, Y., Ionescu-Matiu, I., Sparrow, J. T., Six, H. R., Peterson, D. L., Hollinger, F. B. and Melnick, J. L. (1982) Antibody to hepatitis B surface antigen after a single inoculation of uncoupled synthetic HBsAg peptides Nature 295, 158–160

Edman, J. C., Hallewell, R. A., Valenzuela, P., Goodman, H. M. and Rutter, W. J. (1981) Synthesis of hepatitis B surface and core antigens in E. Coli. Nature 291, 503–506.

Goodfriend, T. L., Levine, L. and Fasman, G. D. (1964) Antibodies to pradykinin and angiotensin: A use of carbodiimides in immunology. Science 144, 1344–1346.

Hopp, T. P. (1981) A synthetic peptide with hepatitis B surface antigen reactivity. Mol. Immunol. 18, 869–872.

Hopp, T. P. and Woods, K. R. (1981) Prediction of protein antigenic determinants from amino acid sequences. Proc. Natl. Acad. Sci. U.S.A. 78, 3824–3828.

Kito, Y., Satomi, M., Ukawa, K. and Akit, T. (1980) Efficient deprotection of $N^G$ tosyl-arginine with a thioanisol-trifluoromethane sulfonic acid system. J.C.S.Che.M.Commun. 1063–1064.

Lerner, R. A., Green, N., Alexander, H., Liu, F.-T, Sutcliffe, J. G. and Shinnick, T. M. (1981) Chemically synthesized peptides predicted from the nucleotide sequence of the hepatitis B virus genome elicit antibodies reactive with the native envelope protein of Dane particles. Proc. Natl. Acad. Sci. U.S.A. 78, 3403–3407.

Mackay, P., Pasek, M., Magazin, M., Kovacic, R. T., Allet, B., Stahl, S., Gilbert, W., Schaller, H., Bruce, S. A. and Murray, K. (1981) Production of immunogenically active surface antigens of hepatitis B virus by Escherichia Coli. Proc. Natl. Acad. Sci. U.S.A. 78, 4510–4514.

McAuliffe, V. J., Purcell, R. H. and Gerin, J. L. (1980) Type B hepatitis: A review of current prospects for a safe and effective Vaccine. Rev. Infect. Dis. 2, 470–492.

Nash, H., Talwar, G. P., Segal, S., Luukkainen, T., Jehansson, E. D. B., Vasquez, J., Coutinho, E. and Sudaram K. (1980) Observations on the antigenicity and clinical effects of a chorionic gonadotropin linked to tetanus toxoid. Fertility and Sterility 34, 328–335.

Prince, A. M., Ikram, H. and Hopp, T. P. (1982) Hepatitis B Virus Vaccine; Identification of HBsAg/a and HBsAg/d but not HBsAg/Y subtype antigenic determinants on a synthetic immunogenic peptide. Proc. Natl. Acad. Sci. U.S.A. 79, 579–582.

Valenzuela, P., Medina, A., Rutter, W. J. Ammerer, G. and Hall, B. D. (1982) Synthesis and assembly of hepatitis B virus surface antigen particles in yeast. Nature 298, 347–350.

Vyas, G. N. (1981) Molecular immunology of the hepatitis B surface antigen (HBsAg). in *Hepatitis B Vaccine* (Edited by Maupas, P and Guesry, P.), P. 227, Elsevier, Amsterdam.

Wainfan, B. (1976) Computer Analysis of quantitative anti-HBs determination by the AUSAB procedure. Computer Programs in Biomed. 6, 243–248.

What is claimed is:

1. A synthetic peptide consisting essentially of the following sequence of amino acids
   Arg Trp Met Met Leu Arg Arg.

2. A synthetic peptide consisting essentially of the following sequence of amino acids
   Gly Tyr Arg Trp Met Met Leu Arg Arg Phe Gly.

* * * * *

UNITED STATES PATENT AND TRADEMARK OFFICE
CERTIFICATE OF CORRECTION

PATENT NO. : 4,578,217

DATED : March 25, 1986

INVENTOR(S) : John Vnek, et al.

It is certified that error appears in the above-identified patent and that said Letters Patent is hereby corrected as shown below:

| | |
|---|---|
| Col. 3, line 29 | Delete "States" and substitute --Stated-- |
| Col. 4, line 59 | Delete "the reby" and substitute --hereby-- |
| Col. 6, line 56 | After "reacting" delete "the" and substitute --with-- |
| Col. 7, line 9 | After "suitable" insert --large-- |
| Col. 8, line 51-52 | Delete "suitabe" and substitute --suited-- |
| Col. 9, line 5 | After "specific" delete "component" and substitute --composition-- |
| Col. 11, line 32 | Correct spelling of --individual-- |

Signed and Sealed this

Twenty-second Day of July 1986

[SEAL]

Attest:

DONALD J. QUIGG

Attesting Officer

Commissioner of Patents and Trademarks